United States Patent
Wieser et al.

(10) Patent No.: US 9,534,004 B2
(45) Date of Patent: Jan. 3, 2017

(54) CRYSTALLINE FORMS OF CEFTAROLINE FOSAMIL

(71) Applicant: Sandoz AG, Basel (CH)

(72) Inventors: Josef Wieser, Kundl (AT); Hubert Sturm, Kundl (AT); Arthur Pichler, Kundl (AT); Andreas Hotter, Kundl (AT); Nolwenn Martin, Kundl (FR); Christoph Langes, Innsbruck (AT); Ulrich Griesser, Innsbruck (AT)

(73) Assignee: SANDOZ AG, Basel (CH)

( * ) Notice: Subject to any disclaimer, the term of this patent is extended or adjusted under 35 U.S.C. 154(b) by 0 days.

(21) Appl. No.: 14/653,122

(22) PCT Filed: Dec. 19, 2013

(86) PCT No.: PCT/EP2013/077350
§ 371 (c)(1),
(2) Date: Jun. 17, 2015

(87) PCT Pub. No.: WO2014/096176
PCT Pub. Date: Jun. 26, 2014

(65) Prior Publication Data
US 2016/0200750 A1 Jul. 14, 2016

(30) Foreign Application Priority Data
Dec. 20, 2012 (EP) .................... 12198649

(51) Int. Cl.
C07F 9/6561 (2006.01)

(52) U.S. Cl.
CPC ......... C07F 9/6561 (2013.01); C07F 9/65613 (2013.01)

(58) Field of Classification Search
CPC .................................. C07F 9/65613
USPC ........................... 540/225; 514/80
See application file for complete search history.

(56) References Cited

FOREIGN PATENT DOCUMENTS

| EP | 1043327 A1 | 10/2000 | |
|---|---|---|---|
| EP | 1310502 A1 * | 5/2003 | ........... A61K 31/675 |
| JP | 2003 300985 | 10/2003 | |
| WO | 2010/025328 | 3/2010 | |
| WO | 2014/060202 A1 | 4/2014 | |

OTHER PUBLICATIONS

Caira, "Crystallie Polymorphism of Organic Compounds," Topics in current chemistry, Springer, Berlin, De, vol. 198,Jan. 1, 1998, pp. 164-208.
International Search Report Issued in PCT/EP2013/077350, Feb. 19, 2014, pp. 1-2.
Ishikawa, Tak-599, a novel n-phosphono type prodrug of anit-mrsa cephalosporin T-91825: synthesis, physicochemical and pharmacological properties, Biorg. Med. Chem. 11 (2003) pp. 2427-2437.
International Search Report issued in PCT/EP2013/070200, Apr. 12, 2013, pp. 1-4.
Copending U.S. Appl. No. 14/436,493, filed Apr. 27, 2015.
Response filed in European patent application No. 13 819 025.1 on Mar. 3, 2016, pp. 1-6.
Labconco, "A guide to freeze drying," Labconco Corporation, www.labconco.com, 2004, pp. 1-12.

* cited by examiner

Primary Examiner — Kahsay Habte
(74) Attorney, Agent, or Firm — Jeffrey S. Melcher; Manelli Selter PLLC

(57) ABSTRACT

The present invention relates to novel crystalline forms of ceftaroline fosamil and to methods for their preparation. Furthermore the present invention relates to the use of the novel forms of ceftaroline fosamil for the preparation of an antibiotic medicament. In addition the present invention relates to pharmaceutical compositions comprising an effective amount of the novel forms of ceftaroline fosamil and to methods of preparing the same. Finally the present invention relates to pharmaceutical combinations comprising an effective amount of the novel forms of ceftaroline fosamil and β-lactamase inhibitors.

16 Claims, 7 Drawing Sheets

CRYSTALLINE FORMS OF CEFTAROLINE FOSAMIL

FIELD OF THE INVENTION

The present invention relates to novel crystalline forms of ceftaroline fosamil and to methods for their preparation. Furthermore the present invention relates to the use of the novel forms of ceftaroline fosamil for the preparation of an antibiotic medicament. In addition the present invention relates to pharmaceutical compositions comprising an effective amount of the novel forms of ceftaroline fosamil and to methods of preparing the same. Finally the present invention relates to pharmaceutical combinations comprising an effective amount of the novel forms of ceftaroline fosamil and β-lactamase inhibitors.

BACKGROUND OF THE INVENTION

Polymorphism and pseudopolymorphism (polymorphism of solvates and hydrates respectively) are phenomenons relating to the occurrence of different crystal forms for one molecule. There may be several different crystalline forms for the same molecule with distinct crystal structures and varying in physical properties like melting point, XRPD pattern and FTIR spectrum. These different crystalline forms are thus distinct solid forms which share the molecular formula of the compound from which the crystals are made up, however they may have distinct physical properties such as e.g. chemical stability, physical stability, hygroscopicity, solubility, dissolution rate, bioavailability, flowability, compressibility, pKa-value, residual solvent content, etc.

Ceftaroline fosamil, 4-[2-[[[(6R,7R)-2-carboxy-7-[[(2Z)-2-(ethoxyimino)-2-[5-(phosphonoamino)-1,2,4-thiadiazol-3-yl]acetyl]amino]-8-oxo-5-thia-1-azabicyclo[4.2.0]oct-2-en-3-yl]thio]-4-thiazolyl]-1-methylpyridinium, is a prodrug with improved solubility compared to its active metabolite ceftaroline. Within the β-lectern antibiotics ceftaroline fosamil belongs to the subclass of cephalosporins and is indicated for the treatment of community-acquired bacterial pneumonia (CABP) as well as acute bacterial skin and skin structure infections. The product received marketing approval in the US (brand name Teflaro®) and is represented by the following formula (I):

EP1043327 A1 discloses amongst others ceftaroline fosamil per se in lyophilized non-crystalline form.

EP1310502 A1 discloses amongst others different crystalline forms of ceftaroline fosamil such as an acetic acid solvate monohydrate, a propionic acid solvate monohydrate and an acetonitrile solvate. Acetonitrile is a class 2 solvent and its content in pharmaceutical products is limited to 410 ppm (ICH Steering Committee, Guideline for Residual Solvents, 17.07.1997). Hence, the ceftaroline fosamil acetonitrile solvate disclosed in EP1310502 A1 is no suitable form for the preparation of a medicament as the acetonitrile amount of this crystalline form exceeds the limit significantly.

Both ceftaroline fosamil acetic acid solvate monohydrate and ceftaroline fosamil propionic acid solvate monohydrate of EP1310502 A1 contain carbon acids in their crystal structure. These carbon acids are partially replaced by water at increased relative humidities leading to a decreased carbon acid amount which finally affects the pKa of the drug substance and consequently the pH of the thereof prepared solution. Consequently in order to avoid batch-wise adjusting of the pH adjusting excipient, ceftaroline fosamil acetic acid solvate monohydrate and ceftaroline fosamil propionic acid solvate monohydrate of EP1310502 A1 need to be stored at low relative humidities in order to ensure a constant carbon acid amount and therefore a constant pKa value of the drug substance.

Ceftaroline fosamil is marketed as monoacetate monohydrate in form of a powder for reconstitution whereat the compound is blended with L-arginine as pH adjusting excipient in order to adjust a specific pH which is required for complete dissolution of the drug substance.

OBJECTIVE OF THE INVENTION

Hence aim of the present invention is to provide improved forms of ceftaroline fosamil, that in particular circumvent the drawbacks of the known forms of ceftaroline fosamil by providing crystalline forms of ceftaroline fosamil which have a constant pKa value over a broad range of relative humidities and consequently do not ask for e.g. controlled and expensive storage conditions or special and expensive packaging.

SUMMARY OF THE INVENTION

Object of the present invention is crystalline ceftaroline fosamil according to formula (II)

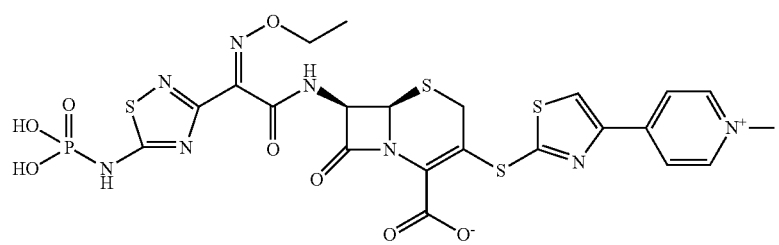

(I)

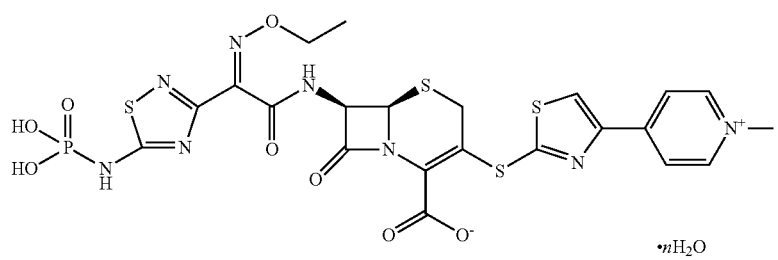

(II)

·nH₂O wherein n is 0 to 5 and preferably 0.1 to 5.

Crystalline ceftaroline fosamil according to the invention is preferably a pure hydrate and not a mixed solvate with another solvent.

Preferably the crystalline ceftaroline fosamil according to the invention is essentially free of carbonic acids and organic nitriles, in particular acetic acid, propionic acid and acetonitrile. Preferably the content of carbonic acids, in particular acetic acid and propionic acid, is below 0.5% (w/w), more preferably below 0.1% (w/w), even more preferred 0.02% (w/w). Preferably the content of organic nitriles, in particular acetonitrile, is below 410 ppm, more preferably below 200 ppm, even more preferred 100 ppm.

Advantageously the amounts of residual solvents in the the crystalline ceftaroline fosamil according to the invention are well within the allowed ICH-limits and therefore crystalline ceftaroline fosamil according to the invention is suitable for the preparation of a pharmaceutical composition, such as a powder for injection.

Advantageously ceftaroline fosamil of the present invention only shows variations in the water content when stored at different relative humidities and therefore do not require controlled and expensive storage conditions or special packaging as the pKa of the drug substance is not affected.

Preferred crystalline forms according to the present invention are herein referred to as forms H and D.

In particular the inventors of the present invention have found novel crystalline forms of ceftaroline fosamil, in the following named ceftaroline fosamil forms H and D. Forms H and D show advantageous properties making them especially suitable for the preparation of a medicament.

In a preferred embodiment the present invention relates to a novel crystalline form of ceftaroline fosamil, in the following named ceftaroline fosamil form H. Form H has preferably 2.5 to 5 molecules of crystal water per molecule ceftaroline fosamil—n in formula (II) being preferably in a range from 2.5 to 5. Form H of ceftaroline fosamil can be characterized by an X-ray powder diffractogram comprising characteristic peaks at 2-theta angles of 5.7±0.2°, 6.9±0.2°, 11.9±0.2°, 19.3±0.2° and 23.6±0.2°. The X-ray powder diffractogram of form H of ceftaroline fosamil comprises additional characteristic peaks at 2-theta angles of 4.8±0.2°, 9.6±0.2°, 11.5±0.2°, 13.8±0.2° and 17.1±0.2°. The X-ray powder diffractogram values refer to a measurement at 40% relative humidity (RH).

In a further preferred embodiment the present invention relates to a process of preparing form H of ceftaroline fosamil comprising the steps of
  a) suspending ceftaroline fosamil in water,
  b) adding seed crystals to the suspension,
  c) slurrying the suspension until the transformation to form H is complete,
  d) isolating the solid material and
  e) drying the material.

The seed crystals can be either obtained from commercially available ceftaroline fosamil or from previously obtained ceftaroline fosamil form H crystals. In addition the present invention relates to a process of preparing form H seed crystals comprising exposing ceftaroline fosamil acetic acid solvate monohydrate (e.g. as prepared according to EP1310502 A1) to a moisture sorption/desorption procedure.

In another preferred embodiment the present invention relates to a novel crystalline form of ceftaroline fosamil, in the following named ceftaroline fosamil form D. Form D has preferably 0.1 to 2 molecules of crystal water per molecule ceftaroline fosamil—n in formula (II) being preferably in a range from 0.1 to 2. Form D of ceftaroline fosamil can be characterized by an X-ray powder diffractogram comprising characteristic peaks at 2-theta angles of 5.2±0.2°, 6.6±0.2°, 17.0±0.2°, 19.2±0.2° and 21.9±0.2° preferably measured at 40% RH. The X-ray powder diffractogram of form D of ceftaroline fosamil comprises additional characteristic peaks at 2-theta angles of 7.7±0.2°, 8.2±0.2°, 10.7±0.2°, 12.9±0.2° and 13.9±0.2° preferably measured at 40% RH.

In a further preferred embodiment the present invention relates to a process of preparing form D of ceftaroline fosamil comprising the steps of
  a) slurrying ceftaroline fosamil in a mixture of aqueous ethanol and hydrochloric acid until form D is obtained,
  b) isolating the solid material and
  c) drying the material.

Furthermore the present invention relates to the use of the novel crystalline forms H and/or D of ceftaroline fosamil for the preparation of an antibiotic medicament.

In addition the present invention relates to pharmaceutical compositions comprising an effective amount of the novel crystalline forms H and/or D of ceftaroline fosamil and at least one pharmaceutically acceptable excipient and to methods of preparing the same.

Finally the present invention relates to pharmaceutical combinations comprising an effective amount of the novel forms H and/or D of ceftaroline fosamil and at least one β-lactamase inhibitor.

In the context of the present invention the following abbreviations have the indicated meaning, unless explicitly stated otherwise:
XRPD: X-ray powder diffractogram
FTIR: Fourier transform infrared
RH: relative humidity
ICH: International conference on harmonisation of technical requirements for registration of pharmaceuticals for human use

DETAILED DESCRIPTION OF THE INVENTION

As used herein the term "room temperature" indicates that the applied temperature is not critical and that no exact temperature value has to be kept. Usually, "room temperature" is understood to mean temperatures of about 15° C. to about 25° C. [see e.g. EU Pharmacopoeia 7.5, 1.2 (2012)].

In a first aspect the present invention relates to a novel crystalline form of ceftaroline fosamil (hereinafter also referred to as ceftaroline fosamil form H).

Ceftaroline fosamil form H of the present invention is present as a single stereoisomer with 6R, 7R configuration.

Figure 1:
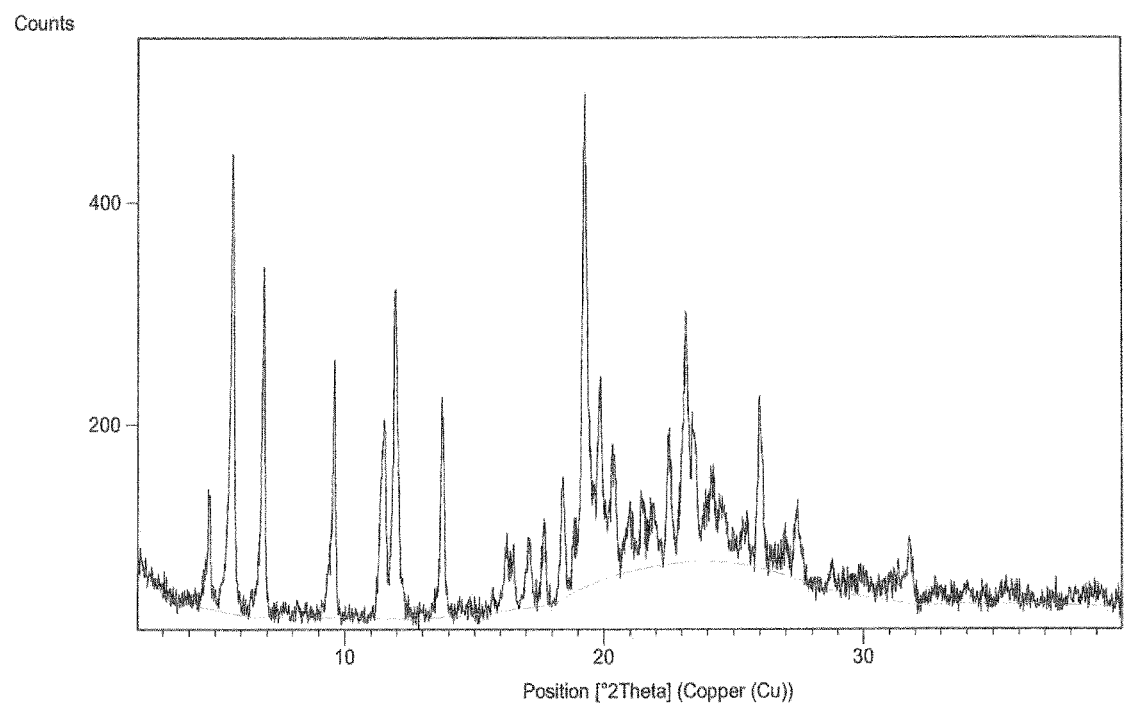
FIG. 1: XRPD of ceftaroline fosamil form H.

Form H of ceftaroline fosamil can be characterized by an X-ray powder diffractogram comprising characteristic peaks at 2-theta angles of 5.7±0.2°, 6.9±0.2°, 11.9±0.2°, 19.3±0.2° and 23.6±0.2° measured at 40% RH. The X-ray powder diffractogram of form H of ceftaroline fosamil comprises additional characteristic peaks at 2-theta angles of 4.8±0.2°, 9.6±0.2°, 11.5±0.2°, 13.8±0.2° and 17.1±0.2° measured at 40% RH. A representative diffractogram is displayed in FIG. 1.

Figure 5:
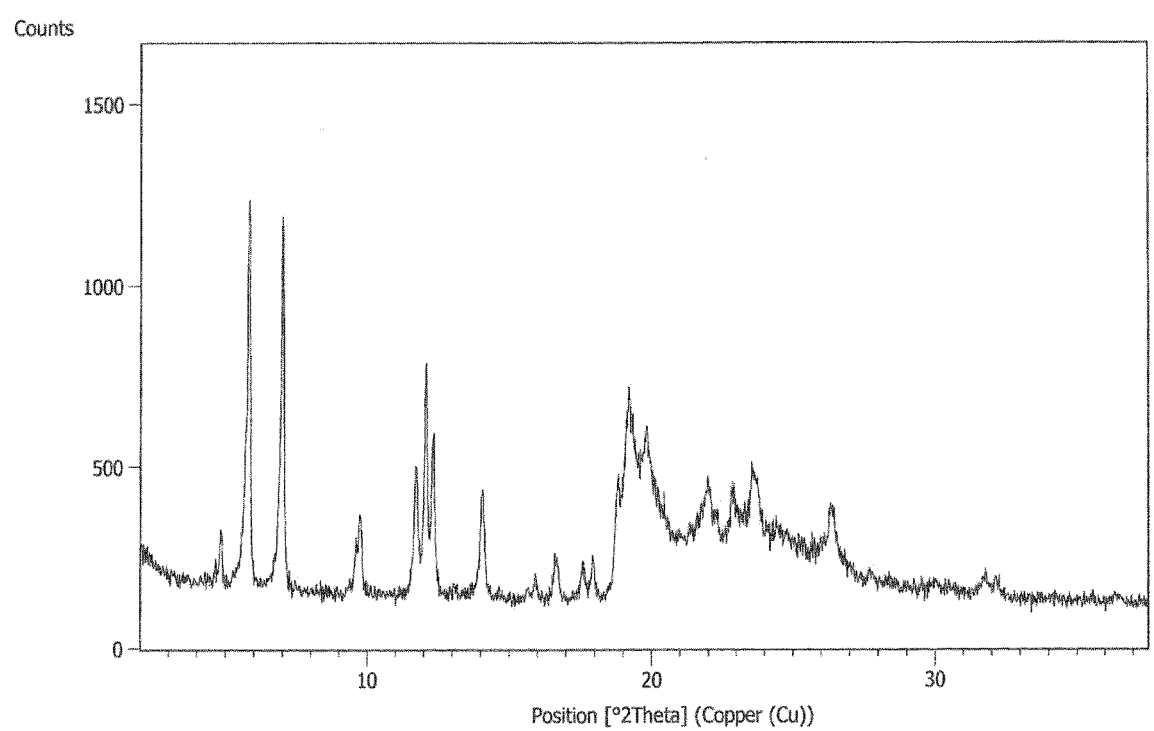
FIG. 5: XRPD of ceftaroline fosamil form H recorded during the sorptive cycle of a humidity and temperature controlled experiment at 25° C., 40% RH.
Figure 6:
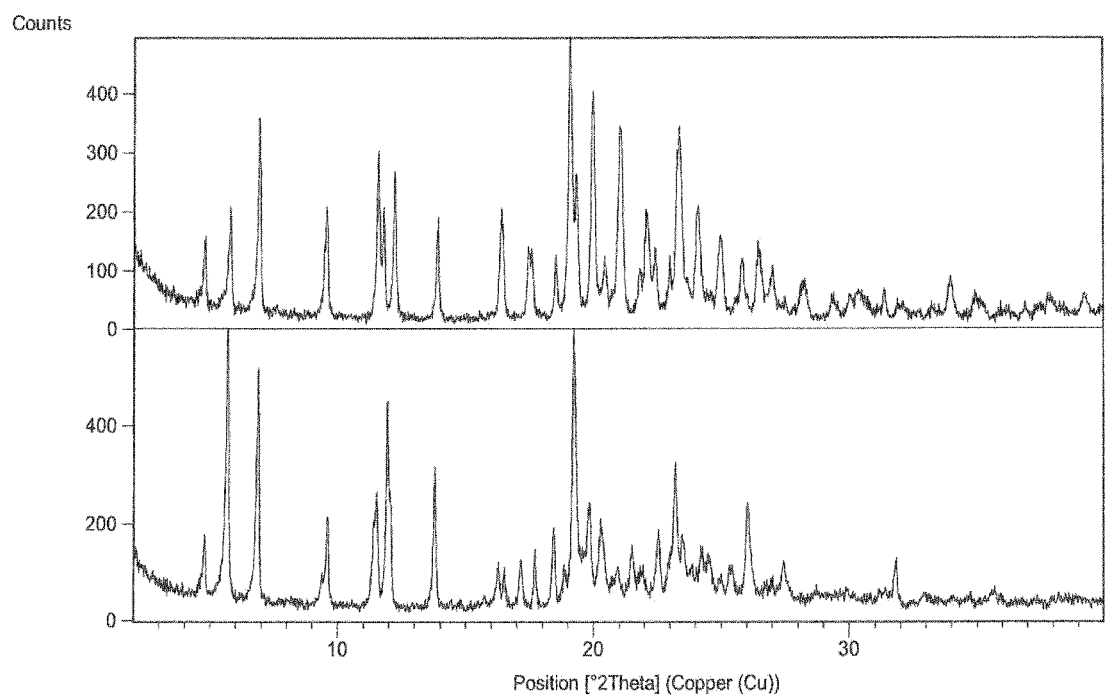
FIG. 6: XRPD overlay of ceftaroline fosamil acetic acid solvate monohydrate before (top) and after (bottom) a sorption-desorption cycle experiment as described in example 1.
Figure 7:
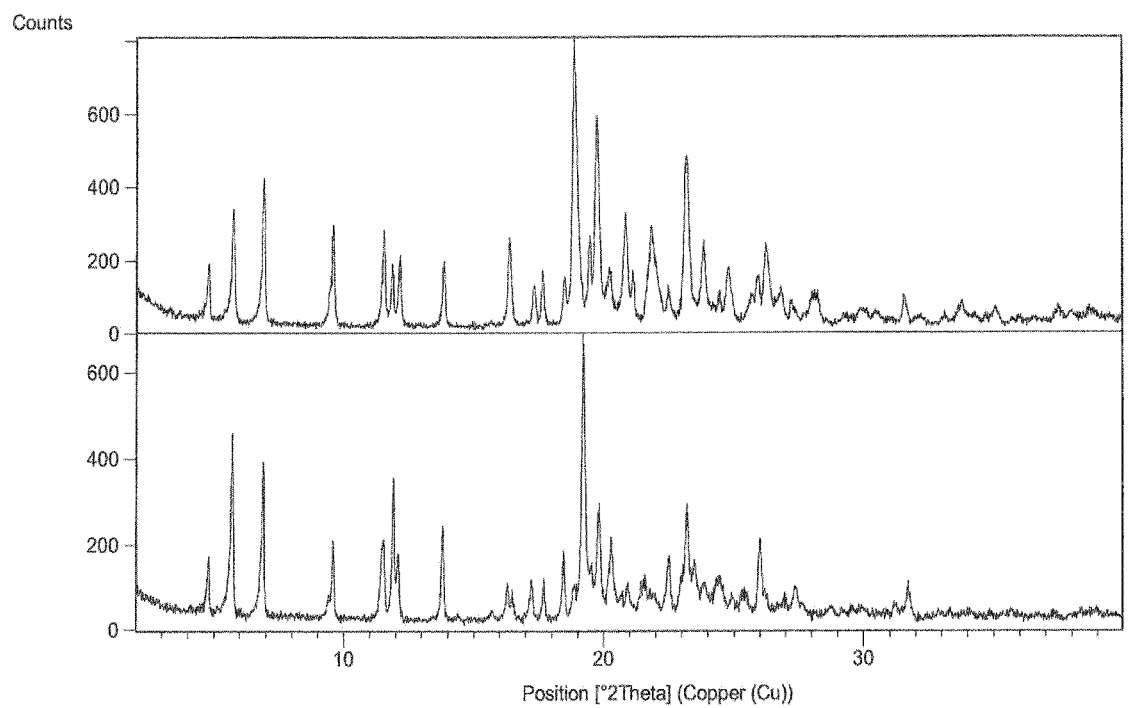
FIG. 7: XRPD overlay of ceftaroline fosamil propionic acid solvate monohydrate before and after a sorption-desorption cycle experiment as described in example 1.

The positions of certain XRPD peaks of form H change when varying the RH between 0 and 90%. XRPD measurements in this range show anisotropic peak shifts to higher 2-theta angles on drying, which are reversible when increasing the relative humidity. These shifts are due to the shrinkage respectively the expansion of the unit cell caused by humidity dependent water contents in the sample. Since the shifts are reversible a phase transformation can be excluded. Table 1 lists some characteristic XRPD peaks from diffractograms recorded at increasing relative humidities during the sorptive cycle of the experiment. A diffractogram recorded at 40% RH during these examinations is shown in FIG. 5.

TABLE 1

| Characteristic XRPD peaks of form H at different relative humidities | | | | | |
|---|---|---|---|---|---|
| 0% RH | 6.0 | 7.2 | 12.3 | 19.9 | 24.3 |
| 10% RH | 6.0 | 7.2 | 12.2 | 19.8 | 24.1 |
| 20% RH | 5.9 | 7.1 | 12.2 | 19.3 | 23.9 |
| 30% RH | 5.9 | 7.0 | 12.1 | 19.3 | 23.7 |
| 40% RH | 5.8 | 7.0 | 12.1 | 19.2 | 23.6 |
| 50% RH | 5.8 | 7.0 | 12.0 | 19.2 | 23.5 |
| 60% RH | 5.7 | 6.9 | 12.0 | 19.2 | 23.4 |
| 70% RH | 5.7 | 6.9 | 12.0 | 19.2 | 23.3 |
| 80% RH | 5.7 | 6.9 | 12.0 | 19.2 | 23.2 |
| 90% RH | 5.7 | 6.9 | 12.0 | 19.2 | 23.2 |

Figure 2:
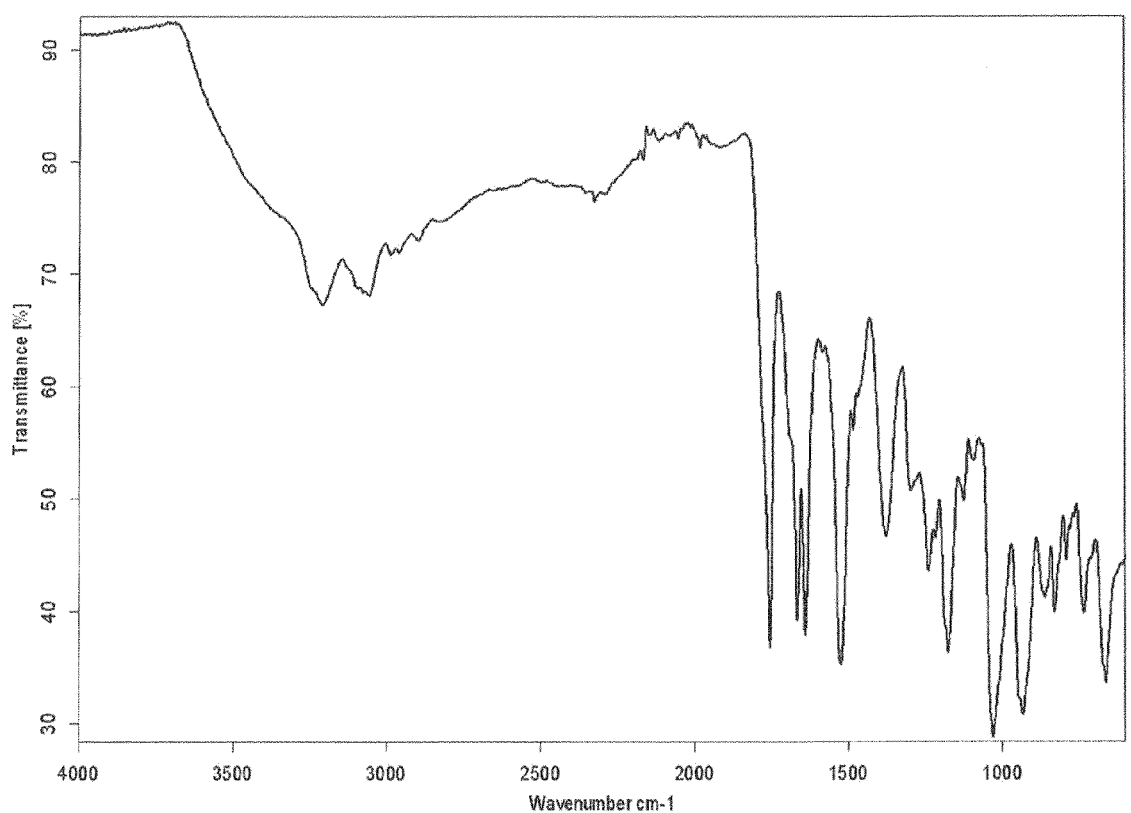
FIG. 2: FTIR spectrum of ceftaroline fosamil form H.

In addition or alternatively form H of ceftaroline fosamil can be characterized by showing an FTIR-spectrum comprising peaks at wavenumbers of 3207±2 cm$^{-1}$, 1753±2 cm$^{-1}$, 1525±2 cm$^{-1}$, 1376±2 cm$^{-1}$ and 934±2 cm$^{-1}$. The FTIR-spectrum of form H of ceftaroline fosamil comprises additional characteristic peaks at wavenumbers of 1665±2 cm$^{-1}$, 1638±2 cm$^{-1}$, 1175±2 cm$^{-1}$, 1030±2 cm$^{-1}$ and 664±2 cm$^{-1}$. A representative FTIR spectrum is displayed in FIG. 2.

The present invention also relates to a process of preparing form H of ceftaroline fosamil comprising the steps of
a) suspending ceftaroline fosamil in water,
b) adding form H seeds to the suspension,
c) slurrying the suspension until complete transformation to form H,
d) isolating the solid material and
e) drying the material.

In a first step a suspension of ceftaroline fosamil in water is prepared. Suitable forms which may be applied in step a) of the above describe process are e.g. ceftaroline fosamil acetic acid solvate monohydrate and ceftaroline fosamil propionic acid solvate monohydrate of EP1310502 A1 or mixtures thereof.

The initial ceftaroline fosamil concentration in step a) of the process is chosen such that the material does not dissolve completely and that a homogenous suspension is obtained. The initial ceftaroline fosamil concentration applied may preferably range from about 10 to 300 g/L, more preferably from about 30 to 200 g/L and most preferably from about 50 to 100 g/L.

To the obtained aqueous suspension form H seeds are added in step b) of the process. The amount of seeds may preferably range from about 1 to 20 weight %, more preferably from about 1 to 10 weight % and most preferably from about 1 to 5 weight %.

Thereafter the suspension is stirred at a temperature preferably ranging from about 0 to 40° C., more preferably from about 10 to 30° C. and most preferably the suspension is stirred at about room temperature until the transformation to form H is complete. Typically, dependent on the applied temperature, several minutes to several hours are required to complete the transformation, e.g. at room temperature the transformation is complete in less than 3 hours. The transformation may be monitored by classical methods such as XRPD.

After complete transformation the form H crystals are collected by any conventional methods such as filtration or centrifugation, most preferably by filtration. An additional washing step may also be applied by rinsing the crystals with water and/or slurrying the crystals in water.

Finally the crystals are dried preferably under vacuum at a temperature preferably ranging from about 20 to 50° C., more preferably from about 20 to 40° C. and most preferably at about room temperature for a time preferably ranging from about 2 to 72 hours, more preferably from about 4 to 48 hours and most preferably from about 6 to 24 hours.

In the above disclosed process for form H production seed crystals are applied. Hence the present invention relates to a process of preparing form H seed crystals in pure crystalline form comprising exposing ceftaroline fosamil acetic acid solvate monohydrate of EP1310502 A1 to a sophisticated gravimetric moisture sorption/desorption experiment. E.g. ceftaroline fosamil acetic acid solvate monohydrate is exposed to 30% RH, the RH humidity is then decreased to 3%, increased to 5% and then in 5% steps increased to 90% RH, decreased in 5% steps to 0% RH, increased in 5% steps to 95% RH, decreased to 90% and finally decreased in 10% steps to 40% RH (at 25° C.). The form H seeds are obtained in pure crystalline form according to this procedure and can be applied in the herein described process for form H production.

In a second aspect the present invention relates to a novel crystalline form of ceftaroline fosamil (hereinafter also referred to as ceftaroline fosamil form D).

Figure 3:
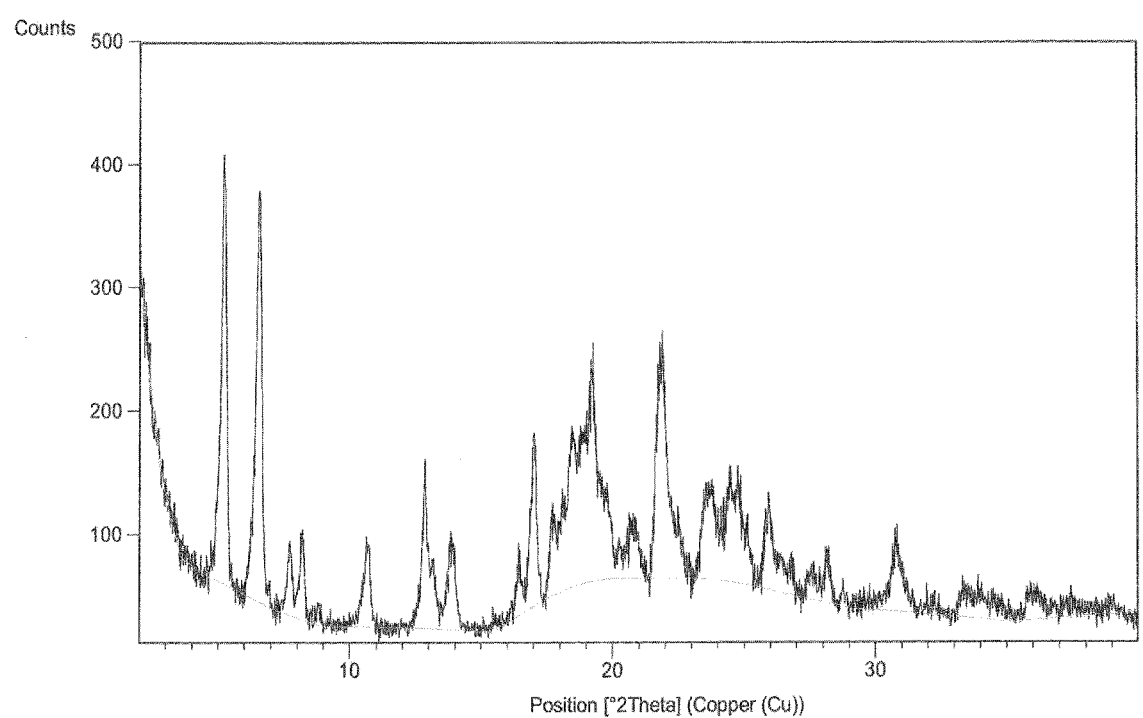
FIG. 3: XRPD of ceftaroline fosamil form D.

Ceftaroline fosamil form D of the present invention is present as a single stereoisomer with 6R, 7R configuration. Form D of ceftaroline fosamil can be characterized by an X-ray powder diffractogram comprising characteristic peaks at 2-theta angles of 5.2±0.2°, 6.6±0.2°, 17.0±0.2°, 19.2±0.2° and 21.9±0.2° preferably measured at 40% RH. The X-ray powder diffractogram of form D of ceftaroline fosamil comprises additional characteristic peaks at 2-theta angles of 7.7±0.2°, 8.2±0.2°, 10.7±0.2°, 12.9±0.2° and 13.9±0.2° preferably measured at 40% RH. A representative diffractogram is displayed in FIG. 3.

Contrary to the XRPD of form H no peak shifts are observed in the diffractograms of form D when increasing or decreasing the RH levels, even though this form also takes up respectively releases water according to the relative humidity.

Figure 4:
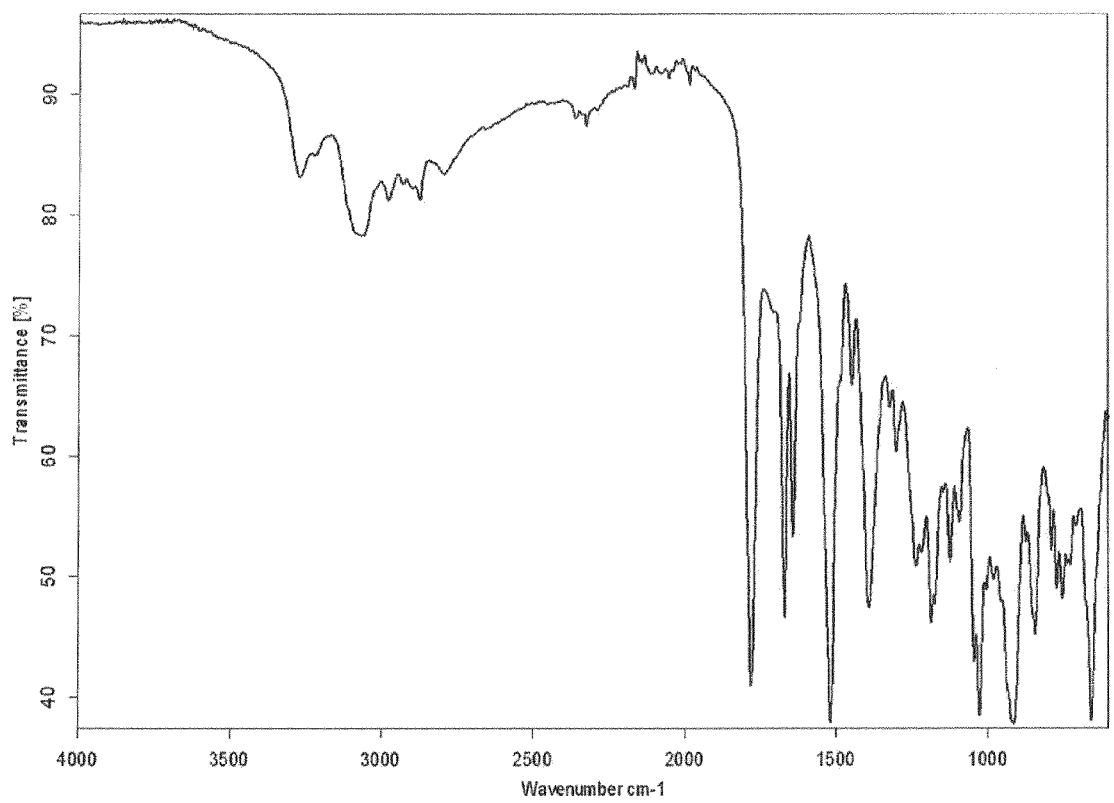
FIG. 4: FTIR spectrum of ceftaroline fosamil form D.

In addition or alternatively form D of ceftaroline fosamil can be characterized by showing an FTIR-spectrum comprising peaks at wavenumbers of 3273±2 $cm^{-1}$, 1782±2 $cm^{-1}$, 1520±2 $cm^{-1}$, 1393±2 $cm^{-1}$ and 916±2 $cm^{-1}$. The FTIR-spectrum of form D of ceftaroline fosamil comprises additional characteristic peaks at wavenumbers of 1671±2 $cm^{-1}$, 1643±2 $cm^{-1}$, 1188±2 $cm^{-1}$, 845±2 $cm^{-1}$ and 660±2 $cm^{-1}$. A representative FTIR spectrum is displayed in FIG. 4.

The present invention also relates to a process for the preparation of form D of ceftaroline fosamil comprising the steps of
 a) slurrying ceftaroline fosamil in a mixture of aqueous ethanol and hydrochloric acid until form D is obtained,
 b) isolating form D and
 c) drying the material.

In a first step a suspension of ceftaroline fosamil in aqueous ethanol and hydrochloric acid is prepared. Suitable forms which may be applied in step a) of the above describe process are e.g. ceftaroline fosamil acetic acid solvate monohydrate and ceftaroline fosamil propionic acid solvate monohydrate of EP1310502 A1 or mixtures thereof.

The initial ceftaroline fosamil concentration in step a) of the process is chosen such that the material does not dissolve completely and that a homogenous suspension is obtained. The initial ceftaroline fosamil concentration applied may preferably range from about 10 to 300 g/L, more preferably from about 30 to 200 g/L and most preferably from about 50 to 100 g/L.

Preferably the aqueous ethanol is used at a concentration ranging from about 1 to 80 volume %, more preferably from about 1 to 70 volume % and most preferably from about 1 to 65 volume %.

Preferably about 0.5 to 2.0 volume %, more preferably about 0.7 to 1.8 volume % and most preferably about 1.0 to 1.5 volume % concentrated hydrochloric acid are applied for the preparation of form D. The term concentrated hydrochloric acid means 35 to 38% (w/w) HCl per water.

The obtained suspension is preferably stirred at a temperature ranging from about 0 to 40° C., more preferably from about 0 to 35° C. and most preferably the suspension is stirred from about 0° C. to room temperature. Typically, dependent on the applied temperature, several hours are required to complete the transformation to form D, e.g. at room temperature the transformation is complete within about 12 to 24 hours. The transformation may be monitored by classical methods such as XRPD.

The obtained crystals are then collected by any conventional methods such as filtration, centrifugation or evaporation of the solvent, preferably by filtration. An additional washing step may also be applied by rinsing the crystals with water, ethanol and/or a mixture of water and ethanol and/or slurrying the crystals in water or a mixture of water and ethanol, whereat the ratio of water and ethanol is preferably the same as the water/ethanol ratio of the mother liquor.

Finally the crystals are dried preferably under vacuum at a temperature preferably ranging from about 20 to 50° C., more preferably from about 20 to 40° C. and most preferably at about room temperature for a time preferably ranging from about 2 to 72 hours, more preferably from about 4 to 48 hours and most preferably from about 6 to 24 hours.

The amounts of residual solvents of the novel forms H and D of ceftaroline fosamil of the present invention are well within the allowed ICH-limits. E.g. for the production of form H of ceftaroline fosamil of the present invention no organic solvent is used as this specific form is obtained from a slurry in water. Form D is obtained from a slurry of ceftaroline fosamil in aqueous ethanol. The ethanol amount in form D was found to be below 0.5% which is well within the allowed limits for residual ethanol. Therefore ceftaroline fosamil forms H and D are suitable forms for the preparation of a medicament.

Advantageously the novel forms D and H of ceftaroline fosamil of the present invention only show variations in their water content when stored at different relative humidities and therefore do not require controlled and expensive storage conditions or special packaging as the pKa of the drug substance is not affected.

Hence aim of the present invention is to circumvent the drawbacks of the known forms of ceftaroline fosamil by providing crystalline forms of ceftaroline fosamil which have a constant pKa value over a broad range of relative humidities and consequently do not ask for e.g. controlled and expensive storage conditions or special and expensive packaging. In addition the amounts of residual solvents in ceftaroline fosamil forms H and D of the present invention are well within the allowed ICH-limits. Therefore the novel forms H and D of ceftaroline fosamil of the present invention are especially suitable for the preparation of a solid pharmaceutical composition, such as a powder for injection.

Consequently the forms H and D of ceftaroline fosamil of the present invention are especially suitable forms for the preparation of an antibiotic composition and may advantageously be employed in various pharmaceutical formulations for use in the treatment of bacterial infection, such as acute bacterial skin and skin structure infections and community-acquired bacterial pneumonia. The present invention therefore also relates to pharmaceutical compositions comprising ceftaroline fosamil form H, form D or mixtures thereof as described above and a pharmaceutically acceptable carrier.

Preferably, the present invention relates to pharmaceutical compositions, wherein more than 95% of ceftaroline fosamil are stably present as ceftaroline fosamil form H and/or form D, more preferably wherein ceftaroline fosamil form H and/or form D are the only detectable crystalline forms of ceftaroline fosamil. The absence of other crystalline forms of ceftaroline fosamil, such as ceftaroline fosamil acetic acid solvate monohydrate, ceftaroline fosamil propionic acid solvate monohydrate or ceftaroline fosamil acetonitrile solvate of EP1310502 A1 can be tested by comparing an XRPD taken of any crystalline ceftaroline fosamil with the XRPD of form H and/or form D as obtained from example 2 respectively from examples 3-5 and shown in FIG. 1 respectively in FIG. 3, which for this comparison are to be taken as XRPDs of 100% form H respectively form D.

"Stably present" as defined herein means that even after storage of the pharmaceutical composition for 180 days, and preferably even after storage for 3 years, the crystalline forms of ceftaroline fosamil designated as ceftaroline fosamil form H and ceftaroline fosamil form D initially comprised in the pharmaceutical composition are still present as ceftaroline fosamil form H respectively ceftaroline fosamil form D after storage for the indicated period.

The pharmaceutical composition of the present invention comprising ceftaroline fosamil form H and/or form D may further comprise one or more pharmaceutically acceptable excipients such as, but not limited to, solubilizing agents.

Examples of suitable solubilizing agents which can also be used for the pharmaceutical composition of the present invention comprising ceftaroline fosamil form H and/or form D are given e.g. in US 2009/0082326 A1, which is herein incorporated by reference, in paragraphs [0028] to [0030]. Specific solubilizing agents, which can also be used for the pharmaceutical composition of the present invention comprising ceftaroline fosamil form H and/or form D include, but are not limited to, formic acid, acetic acid, propionic acid, butyric acid, valeric acid, caproic acid, enanthic acid, caprylic acid, pelargonic acid, capric acid, lauric acid, stearic acid, acrylic acid, decosahexaenoic acid, eicosapentaenoic acid, pyruvic acid, benzoic acid, salicylic acid, aldaric acid, oxalic acid, malonic acid, malic acid, succinic acid, glutaric acid, adipic acid, citric acid, lactic acid, alanine, arginine, asparagine, aspartic acid, cysteine, glutamine, glycine, histidine, isoleucine, leucine, lysine, methionine, phenylalanine, proline, serine, threonine, tryptophan, tyrosine, valine and combinations thereof (including salts thereof and/or individual stereoisomers and/or mixtures of stereoisomers thereof).

Preferred solubilizing agents which can also be used for the pharmaceutical composition of the present invention comprising ceftaroline fosamil form H and/or form D are acetic acid, salts thereof and combinations thereof (e.g. acetic acid/sodium acetate), citric acid, salts thereof and combinations thereof (e.g. citric acid/sodium citrate), DL-arginine and salts thereof (e.g. DL-arginine acetate), L-arginine and salts thereof (e.g. L-arginine acetate) and histidine and salts thereof (e.g. histidine acetate), whereat L-arginine, L-arginine acetate and a combination of L-arginine and L-arginine acetate are most preferred.

A preferred pharmaceutical composition of the present invention comprises ceftaroline fosamil form H and/or form D, L-arginine acetate and L-arginine, wherein the molar ratio of ceftaroline fosamil form H and/or form D (calculated as ceftaroline fosamil anhydrous and non-solvated) to L-arginine acetate to L-arginine preferably is about 1.0:0.5-1.5:0.5-3.0, more preferably about 1.0:0.9-1.1:0.7-2.0 and most preferably about 1.0:1.0:1.0-1.5.

Another preferred pharmaceutical composition of the present invention comprises ceftaroline fosamil form H and/or form D and L-arginine acetate wherein the molar ratio of ceftaroline fosamil form H and/or form D (calculated as ceftaroline fosamil anhydrous and non-solvated) to L-arginine acetate is about 1.0:1.0-4.5, more preferably about 1.0:1.5-3.0 and most preferably about 1.0:2.0-2.5.

The present invention also refers to a process of preparing a pharmaceutical composition comprising ceftaroline fosamil form H and/or form D, wherein ceftaroline fosamil form H and/or form D is mixed with the solubilizing agent in a blender under sterile conditions until a uniform blend is obtained, whereat the solubilizing agent is preferably selected from L-arginine acetate and/or L-arginine. Pre-sterilized vials are then filled with an appropriate amount of the sterile blend. The such obtained sterile blend may then be mixed with a solvent, e.g. water for injection, saline, about 5-10% sugar solution (e.g. glucose, dextrose) and combinations thereof prior to administration. Most preferably water for injection is used as solvent, whereat a volume of about 20 mL is applied resulting in a solution having a pH ranging from about 4.8 to 6.5. The constituted solution must be further diluted in 250 mL before infusion. Appropriate infusion solutions comprise 0.9% sodium chloride injection (normal saline), 5% dextrose injection, 2.5% dextrose injection, 0.45% sodium chloride injection or Lactated Ringer's injection. The resulting solution is then administered intravenously over approximately one hour.

Formulations of the present invention typically comprise 200 to 1200 mg of ceftaroline fosamil form H, form D or mixtures thereof, whereat the preferred dosages are 400 mg and 600 mg (calculated as ceftaroline fosamil anhydrous and non-solvated).

In a further embodiment the present invention relates to a pharmaceutical combination comprising an effective amount of ceftaroline fosamil form H of the present invention, ceftaroline fosamil form D of the present invention or mixtures thereof and one or more β-lactamase inhibitors. Beta-lactamase inhibitors are well known in the state of the art. Although beta-lactamase inhibitors have little antibiotic activity of their own, they instead inhibit the activity of beta-lactamases, a family of enzymes that break the beta-lactam ring of β-lactam antibiotics. Preferably the β-lactamase inhibitors are chosen from but not limited to e.g. clavulanic acid, tazobactam, sulbactam and/or avibactam as disclosed e.g. in U.S. Pat. No. 7,638,529 or U.S. Pat. No. 7,732,610.

Other objects, features, advantages and aspects of the present invention will become apparent to those of skill from the following description. It should be understood, however, that the description and the following specific examples, while indicating preferred embodiments of the invention, are given by way of illustration only. Various changes and modifications within the spirit and scope of the disclosed invention will become readily apparent to those skilled in the art from reading the description and the other parts of the present disclosure.

EXAMPLES

The X-ray powder diffractograms (XRPD) were obtained with a PANalytical X'Pert PRO diffractometer equipped with a theta/theta coupled goniometer in transmission geometry, Cu-Kα1,2 radiation (wavelength 0.15419 nm) with a focusing mirror and a solid state PIXcel detector. The diffractograms were recorded at a tube voltage of 45 kV and a tube current of 40 mA, applying a stepsize of 0.013° 2-Theta with 40 s per step (255 channels) in the angular range of 2° to 40° 2-Theta at ambient conditions. A typical precision of the 2-Theta values is in the range of about ±0.2° 2-Theta. Thus a diffraction peak that appears at 5.0° 2-Theta can appear between 4.8 and 5.2° 2-Theta on most X-ray diffractometers under standard conditions.

For humidity and temperature controlled XRPD measurements samples were equilibrated in a VGI 2000M humidity chamber (SMS, Middlesex UK) with integrated peltier heat pump, circulating fluid pump and water reservoir to ensure uniform temperature distribution and stable sample humidities. RH controlled sorptive and desorptive measurements were recorded between 0%-90% RH+/−0.3% RH in 10% steps with an equilibrium time of 2 hours between consecutive measurements.

Infrared spectra (IR) were recorded on an MKII Golden Gate™ Single Reflection Diamond ATR (attenuated total reflection) cell with a Bruker Tensor 27 FTIR spectrometer with 4 cm$^{-1}$ resolution at ambient conditions. To record a spectrum a spatula tip of a sample was applied to the surface of the diamond in powder form. Then the sample was pressed onto the diamond with a sapphire anvil and the spectrum was recorded. A spectrum of the clean diamond was used as background spectrum. A typical precision of the wavenumber values is in the range of about ±2 cm$^{-1}$. Thus, an infrared peak that appears at 1716 cm$^{-1}$ can appear between 1714 and 1718 cm$^{-1}$ on most infrared spectrometers under standard conditions.

Example 1

Preparation of Ceftaroline Fosamil Form H Seed Crystals

Ceftaroline fosamil acetic acid solvate monohydrate (e.g. prepared according to the procedure described in EP1310502 A1) was applied to the following moisture sorption/desorption cycle using an SPSx-1μ moisture sorption analyzer (Projekt Messtechnik, Ulm, D). The measurement cycle was started at 30% relative humidity (RH), decreased to 3% RH, increased to 5% and then in 5% steps to 90% RH, decreased in 5% steps to 0% RH, increased in 5% steps to 95% RH, decreased to 90% and finally decreased in 10% steps to 40% RH. The time for one step was 3 hours each. The temperature was 25±0.1° C.

Example 2

Preparation of Ceftaroline Fosamil Form H

A suspension of 100 mg ceftaroline fosamil acetic acid solvate monohydrate (e.g. prepared according to the procedure described in EP1310502 A1) in 2 mL water was seeded with 5 mg form H crystals (obtained e.g. by the procedure described in example 1 of the present invention) and stirred at room temperature for about 3 hours. The solid was collected by filtration, washed with water and dried under vacuum at room temperature for about 7 hours to obtain crystalline form H of ceftaroline fosamil.

TABLE 2

XRPD angles 2-Theta and relative intensities of ceftaroline fosamil form H

| angle [2-Theta] | relative intensity [%] |
|---|---|
| 4.8 | 22 |
| 5.7 | 94 |
| 6.9 | 71 |
| 9.6 | 52 |
| 11.5 | 39 |
| 11.9 | 65 |
| 13.8 | 41 |
| 17.1 | 12 |
| 19.3 | 100 |
| 23.2 | 51 |

TABLE 3

FTIR peaks of ceftaroline fosamil form H wavelength [cm$^{-1}$]

| | |
|---|---|
| 3207 | 1376 |
| 1753 | 1175 |
| 1665 | 1030 |
| 1638 | 934 |
| 1525 | 664 |

Example 3

Preparation of Ceftaroline Fosamil Form D

A suspension of 2.00 g ceftaroline fosamil acetic acid solvate monohydrate (e.g. prepared according to the procedure described in EP1310502 A1) in 21 mL ethanol/water/HCl$_{conc.}$ (1:0.5:0.02=volume:volume:volume) was stirred at room temperature for 23 hours. The solid was collected by filtration and washed with 20 mL water and 20 mL aqueous ethanol (67 volume %). The material was dried at room temperature under vacuum for 5 hours to obtain crystalline form D of ceftaroline fosamil (1.33 g, 68%).

TABLE 4

XRPD angles 2-Theta and relative intensities of ceftaroline fosamil form D

| angle [2-Theta] | relative intensity [%] |
|---|---|
| 5.2 | 100 |
| 6.6 | 96 |
| 7.7 | 17 |
| 8.2 | 19 |
| 10.7 | 18 |
| 12.9 | 38 |
| 13.9 | 20 |
| 17.0 | 39 |
| 19.2 | 50 |
| 21.9 | 51 |

TABLE 5

FTIR peaks of ceftaroline fosamil form D wavelength [cm$^{-1}$]

| | |
|---|---|
| 3273 | 1393 |
| 1782 | 1188 |
| 1671 | 916 |
| 1643 | 845 |
| 1520 | 660 |

Example 4

Preparation of Ceftaroline Fosamil Form D

A suspension of 1.00 g ceftaroline fosamil acetic acid solvate monohydrate (e.g. prepared according to the procedure described in EP1310502 A1) in 10 mL ethanol/water/HCl$_{conc.}$ (1:0.6:0.02=volume:volume:volume) was stirred at room temperature for 18 hours. The solid was collected by filtration and washed with 5 mL aqueous ethanol (50 volume %). The material was dried at room temperature under vacuum for 15 hours to obtain crystalline form D of ceftaroline fosamil.

Example 5

Preparation of Ceftaroline Fosamil Form D

A suspension of 1.80 g ceftaroline fosamil in 20 mL ethanol/water/HCl$_{conc.}$ (1:0.5:0.02=volume:volume:volume) was stirred at room temperature for 23 hours. The solid was collected by filtration and washed with 5 mL aqueous ethanol (67 volume %). The material was dried at room temperature under vacuum for 16 hours to obtain crystalline form D of ceftaroline fosamil (1.31 g, 79%).

Example 6

Formulation with L-Arginine Acetate and L-arginine

| ingredient | amount [mg] |
| --- | --- |
| ceftaroline fosamil form H* | 600 |
| L-arginine acetate | 205 |
| L-arginine | 168 |

*calculated as anhydrous and non-solvated ceftaroline fosamil

Example 7

Formulation with L-Arginine Acetate and L-Arginine

| ingredient | amount [mg] |
| --- | --- |
| ceftaroline fosamil form H* | 400 |
| L-arginine acetate | 137 |
| L-arginine | 112 |

*calculated as anhydrous and non-solvated ceftaroline fosamil

Example 8

Formulation with L-Arginine Acetate and L-arginine

| ingredient | amount [mg] |
| --- | --- |
| ceftaroline fosamil form D* | 600 |
| L-arginine acetate | 205 |
| L-arginine | 168 |

*calculated as anhydrous and non-solvated ceftaroline fosamil

Example 9

Formulation with L-Arginine Acetate and L-arginine

| ingredient | amount [mg] |
| --- | --- |
| ceftaroline fosamil form D* | 400 |
| L-arginine acetate | 137 |
| L-arginine | 112 |

*calculated as anhydrous and non-solvated ceftaroline fosamil

Example 10

Formulation with L-Arginine

| ingredient | amount [mg] |
| --- | --- |
| ceftaroline fosamil form H* | 600 |
| L-arginine | 321 |

*calculated as anhydrous and non-solvated ceftaroline fosamil

Example 11

Formulation with L-Arginine

| ingredient | amount [mg] |
| --- | --- |
| ceftaroline fosamil form H* | 400 |
| L-arginine | 214 |

*calculated as anhydrous and non-solvated ceftaroline fosamil

Example 12

Formulation with L-Arginine

| ingredient | amount [mg] |
| --- | --- |
| ceftaroline fosamil form D* | 600 |
| L-arginine | 321 |

*calculated as anhydrous and non-solvated ceftaroline fosamil

Example 13

Formulation with L-Arginine

| ingredient | amount [mg] |
| --- | --- |
| ceftaroline fosamil form D* | 400 |
| L-arginine | 214 |

*calculated as anhydrous and non-solvated ceftaroline fosamil

Example 14

Formulation with L-Arginine Acetate

| ingredient | amount [mg] |
| --- | --- |
| ceftaroline fosamil form H* | 600 |
| L-arginine acetate | 431 |

*calculated as anhydrous and non-solvated ceftaroline fosamil

Example 15

Formulation with L-Arginine Acetate

| ingredient | amount [mg] |
|---|---|
| ceftaroline fosamil form H* | 400 |
| L-arginine acetate | 287 |

*calculated as anhydrous and non-solvated ceftaroline fosamil

Example 16

Formulation with L-Arginine Acetate

| ingredient | amount [mg] |
|---|---|
| ceftaroline fosamil form D* | 600 |
| L-arginine acetate | 431 |

*calculated as anhydrous and non-solvated ceftaroline fosamil

Example 17

Formulation with L-Arginine Acetate

| ingredient | amount [mg] |
|---|---|
| ceftaroline fosamil form D* | 400 |
| L-arginine acetate | 287 |

The invention claimed is:

1. A crystalline ceftaroline fosamil of formula (II)

[Chemical structure of ceftaroline fosamil] ·$n$H$_2$O  (II)

wherein n is 0.1 to 5.

2. The crystalline form of ceftaroline fosamil according to claim 1 with a maximum content of acetic acid and propionic acid below 0.5% (w/w) and acetonitrile below 410 ppm.

3. The crystalline form of ceftaroline fosamil according to claim 1 having an X-ray powder diffraction pattern comprising peaks at 2-theta angles of 5.7±0.2°, 6.9±0.2°, 11.9±0.2°, 19.3±0.2° and 23.6±0.2°.

4. The crystalline form of ceftaroline fosamil according to claim 1 having an infrared spectrum comprising peaks at wavenumbers of 3207±2 cm$^{-1}$, 1753±2 cm$^{-1}$, 1525±2 cm$^{-1}$, 1376±2 cm$^{-1}$ and 934±2 cm$^{-1}$.

5. A method for the preparation of ceftaroline fosamil according to claim 1 comprising the steps of:
a) suspending ceftaroline fosamil in water;
b) adding seed crystals of ceftaroline fosamil;
c) slurrying the suspension until complete transformation;
d) isolating the solid material; and
e) drying the material.

6. The crystalline form of ceftaroline fosamil according to claim 1 having an X-ray powder diffraction pattern comprising peaks at 2-theta angles of 5.2±0.2°, 6.6±0.2°, 17.0±0.2°, 19.2±0.2° and 21.9±0.2°.

7. The crystalline form of ceftaroline fosamil according to claim 6 having an infrared spectrum comprising peaks at wavenumbers of 3273±2 cm$^{-1}$, 1782±2 cm$^{-1}$, 1520±2 cm$^{-1}$, 1393±2 cm$^{-1}$, and 916±2 cm$^{-1}$.

8. A method for the preparation of the crystalline form of ceftaroline fosamil according to claim 1, comprising the steps of:
a) slurrying ceftaroline fosamil in a mixture of aqueous ethanol and hydrochloric acid until crystals are obtained;
b) isolating the solid material; and
c) drying the material.

9. A pharmaceutical composition comprising:
crystalline ceftaroline fosamil according to claim 1; and
L-arginine or L-arginine acetate.

10. The pharmaceutical composition according to claim 9 wherein the pharmaceutical composition comprises 200 mg to 800 mg, of ceftaroline fosamil calculated as anhydrous and non-solvated ceftaroline fosamil.

11. The pharmaceutical composition according to claim 9 wherein the molar ratio of ceftaroline fosamil, calculated as anhydrous and non-solvated ceftaroline fosamil, to L-arginine acetate to L-arginine is about 1.0:1.0:1.0-1.5.

12. The pharmaceutical composition according to claim 9, which results in a constituted solution having a pH of 4.8 to 6.5.

13. The pharmaceutical combination comprising a crystalline form of ceftaroline fosamil according to claim 1 or mixtures thereof and one or more β-lactamase inhibitors.

14. A method of treating a patient having a bacterial infection comprising administering to the patient a pharmaceutically effective amount of the crystalline ceftaroline fosamil according to claim 1.

15. A method of treating a patient having a bacterial infection comprising administering to the patient a pharmaceutically effective amount of the pharmaceutical composition according to claim 10.

16. The pharmaceutical composition according to claim 9, wherein the pharmaceutical composition comprises 600 mg or 400 mg of ceftaroline fosamil calculated as anhydrous and non-solvated ceftaroline fosamil.

* * * * *